United States Patent
Byrne et al.

(10) Patent No.: US 11,136,528 B2
(45) Date of Patent: Oct. 5, 2021

(54) ESTOLIDES OF VEGETABLE OIL ALKOXYLATES AND METHOD OF MAKING AND USING

(71) Applicant: Indorama Ventures Oxides LLC, The Woodlands, TX (US)

(72) Inventors: Heather Byrne, Houston, TX (US); George Smith, Conroe, TX (US); Hungchang Calvin Chiu, Spring, TX (US); Jeffery Cellura, Spring, TX (US); Xiaohua Fang, Spring, TX (US); Anabel Rubio, Houston, TX (US); Matthew T. Meredith, Spring, TX (US)

(73) Assignee: INDORAMA VENTURES OXIDES LLC, The Woodlands, TX (US)

( * ) Notice: Subject to any disclaimer, the term of this patent is extended or adjusted under 35 U.S.C. 154(b) by 0 days.

(21) Appl. No.: 16/077,358

(22) PCT Filed: Oct. 23, 2017

(86) PCT No.: PCT/US2017/057791
§ 371 (c)(1),
(2) Date: Aug. 10, 2018

(87) PCT Pub. No.: WO2018/085064
PCT Pub. Date: May 11, 2018

(65) Prior Publication Data
US 2020/0362266 A1 Nov. 19, 2020

Related U.S. Application Data

(60) Provisional application No. 62/417,548, filed on Nov. 4, 2016.

(51) Int. Cl.
*C11C 3/06* (2006.01)
*C04B 26/18* (2006.01)
(Continued)

(52) U.S. Cl.
CPC ............... *C11C 3/06* (2013.01); *A01N 25/00* (2013.01); *C04B 26/18* (2013.01); *C10M 145/22* (2013.01); *C11D 3/3715* (2013.01); *C07C 69/675* (2013.01)

(58) Field of Classification Search
CPC ........ C11C 3/00; C11C 3/003; C10M 105/32; C10M 105/40; C10M 2207/2815;
(Continued)

(56) References Cited

U.S. PATENT DOCUMENTS

| 2,785,978 A | 3/1957 | Gracht |
| 4,614,622 A | 9/1986 | Huettinger et al. |

(Continued)

FOREIGN PATENT DOCUMENTS

| EP | 0586323 A | 3/1994 |
| EP | 0667105 A | 8/1995 |

(Continued)

OTHER PUBLICATIONS

Bodalo-Santoyo et al. "Enzymatic biosynthesis of ricinoleic acid estolides", Biochemical Engineering Journal, 2005, vol. 26, Issues 2-3, pp. 155-158.
(Continued)

*Primary Examiner* — Deborah D Carr (57) ABSTRACT

A method of reacting castor oil and an alkoxylated glycerin via a transesterification reaction to produce an estolide of castor oil alkoxylate. Compositions comprising an estolide of castor oil alkoxylate and uses thereof.

20 Claims, 3 Drawing Sheets

(51) Int. Cl.
   *A01N 25/00* (2006.01)
   *C11D 3/37* (2006.01)
   *C10M 145/22* (2006.01)
   *C07C 69/675* (2006.01)

(58) Field of Classification Search
   CPC ............ C10M 2207/2895; C07C 67/08; C07C 69/73; C07C 69/732
   USPC ........................................................ 554/198
   See application file for complete search history.

(56) References Cited

U.S. PATENT DOCUMENTS

| | | | |
|---|---|---|---|
| 4,861,613 A | 8/1989 | White et al. | |
| 4,983,329 A | 1/1991 | Cooper | |
| 5,347,253 A * | 9/1994 | Ogikubo | A63F 9/12 273/239 |
| 5,371,253 A | 12/1994 | Cooper | |
| 5,399,728 A | 3/1995 | Cooper | |
| 5,466,843 A | 11/1995 | Cooper | |
| 5,986,117 A | 11/1999 | Cooper | |
| 6,265,373 B1 | 7/2001 | Oses et al. | |
| RE38,639 E | 10/2004 | Oses et al. | |
| 2011/0282084 A1 | 11/2011 | Potula et al. | |
| 2012/0016039 A1 | 1/2012 | Amari et al. | |
| 2015/0051132 A1 | 2/2015 | Li et al. | |

FOREIGN PATENT DOCUMENTS

| | | |
|---|---|---|
| EP | 0679632 A2 | 11/1995 |
| EP | 0685323 B1 | 12/1997 |
| GB | 723244 A | 2/1955 |
| GB | 2073232 A | 10/1981 |

OTHER PUBLICATIONS

"Safety Assessment of PEGylated Alkyl Glycericdes".

* cited by examiner

ESTOLIDES OF VEGETABLE OIL ALKOXYLATES AND METHOD OF MAKING AND USING

CROSS REFERENCE TO RELATED APPLICATIONS

This application is a National Stage Application filed under 35 U.S.C. 371 of International Application Number PCT/US2017/057791, filed Oct. 23, 2017, which claims the benefit of U.S. Provisional Patent Application Ser. No. 62/417,548, filed Nov. 4, 2016, the entire contents of which are expressly herein incorporated by reference.

STATEMENT REGARDING FEDERALLY SPONSORED RESEARCH OR DEVELOPMENT

Not applicable.

FIELD

The present disclosure generally relates to estolides of vegetable oil alkoxylates and the methods of producing such. In particular, the present disclosure is directed to a method of reacting castor oil and an alkoxylated glycerin via a transesterification reaction to produce an estolide of castor oil alkoxylate. The present disclosure also generally relates to compositions comprising an estolide of castor oil alkoxylate and uses thereof.

BACKGROUND

Typically, vegetable oil alkoxylates are prepared by direct alkoxylation of one or more vegetable oils using base catalysts. The direct alkoxylation process for producing a vegetable oil alkoxylate general comprises (i) reacting a vegetable oil such as coconut oil or palm kernel oil with methanol using a base catalyst to form a methyl ester and removing the glycerin byproduct, (ii) hydrogenating the methyl ester to form an alcohol, and (iii) reacting the alcohol with ethylene oxide ("EO") and/or propylene oxide ("PO") to make the vegetable oil alkoxylate.

For example, EP 0586323 discloses a detergent composition comprising mono-, di-, and tri-ester compounds prepared by direct alkoxylation of coconut oil and palm oil.

Although various references teach the transesterification of vegetable oils and alkoxylated glycerin to form vegetable oil alkoxylates (see, e.g., U.S. RE38,639, US 2012/0016039, U.S. Pat. No. 5,986,117), they fail to teach the presently disclosed and/or claimed estolides of castor oil alkoxylates and the process of producing such.

It is an object of the present disclosure to provide a composition comprising an estolide of castor oil alkoxylate having improved properties over comparable castor oil based alkoxylates produced via direct alkoxylation. It is also an object of the present disclosure to provide compositions comprising an estolide of castor oil alkoxylate as well as compositions and processes that utilize the estolide of castor oil alkoxylate.

DETAILED DESCRIPTION

Before explaining at least one embodiment of the present disclosure in detail, it is to be understood that the present disclosure is not limited in its application to the details of construction and the arrangement of components or steps or methodologies set forth in the following description or illustrated in the drawings. The present disclosure is capable of other embodiments or of being practiced or carried out in various ways. Also, it is to be understood that the phraseology and terminology employed herein is for the purpose of description and should not be regarded as limiting.

Unless otherwise defined herein, technical terms used in connection with the present disclosure shall have the meanings that are commonly understood by those having ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference to the extent that they do not contradict the instant disclosure.

All of the compositions and/or methods disclosed herein can be made and executed without undue experimentation in light of the present disclosure. While the compositions and methods of the present disclosure have been described in terms of preferred embodiments, it will be apparent to those having ordinary skill in the art that variations may be applied to the compositions and/or methods and in the steps or sequences of steps of the methods described herein without departing from the concept, spirit, and scope of the present disclosure. All such similar substitutes and modifications apparent to those skilled in the art are deemed to be within the spirit, scope, and concept of the present disclosure.

As utilized in accordance with the present disclosure, the following terms, unless otherwise indicated, shall be understood to have the following meanings.

The use of the word "a" or "an", when used in conjunction with the term "comprising", "including", "having", or "containing" (or variations of such terms) may mean "one", but it is also consistent with the meaning of "one or more", "at least one", and "one or more than one".

The use of the term "or" is used to mean "and/or" unless clearly indicated to refer solely to alternatives and only if the alternatives are mutually exclusive.

Throughout this disclosure, the term "about" is used to indicate that a value includes the inherent variation of error for the quantifying device, mechanism, or method, or the inherent variation that exists among the subject(s) to be measured. For example, but not by way of limitation, when the term "about" is used, the designated value to which it refers may vary by plus or minus ten percent, or nine percent, or eight percent, or seven percent, or six percent, or five percent, or four percent, or three percent, or two percent, or one percent, or one or more fractions therebetween.

The use of "at least one" will be understood to include one as well as any quantity more than one, including but not limited to, 1, 2, 3, 4, 5, 10, 15, 20, 30, 40, 50, 100, etc. The term "at least one" may extend up to 100 or 1000 or more depending on the term to which it refers. In addition, the quantities of 100/1000 are not to be considered as limiting since lower or higher limits may also produce satisfactory results.

In addition, the phrase "at least one of X, Y, and Z" will be understood to include X alone, Y alone, and Z alone, as well as any combination of X, Y, and Z. Likewise, the phrase "at least one of X and Y" will be understood to include X alone, Y alone, as well as any combination of X and Y. Additionally, it is to be understood that the phrase "at least one of" can be used with any number of components and have the similar meanings as set forth above.

The use of ordinal number terminology (i.e., "first", "second", "third", "fourth", etc.) is solely for the purpose of differentiating between two or more items and, unless otherwise stated, is not meant to imply any sequence or order or importance to one item over another or any order of addition.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The phrases "or combinations thereof" and "and combinations thereof" as used herein refers to all permutations and combinations of the listed items preceding the term. For example, "A, B, C, or combinations thereof" is intended to include at least one of: A, B, C, AB, AC, BC, or ABC and, if order is important in a particular context, also BA, CA, CB, CBA, BCA, ACB, BAC, or CAB. Continuing with this example, expressly included are combinations that contain repeats of one or more items or terms such as BB, AAA, CC, AABB, AACC, ABCCC, CBBAAA, CABBB, and so forth. The skilled artisan will understand that typically there is no limit on the number of items or terms in any combination, unless otherwise apparent from the context. In the same light, the term "and combinations thereof" when used with the phrase "selected from the group consisting of" refers to all permutations and combinations of the listed items preceding the phrase.

The phrases "in one embodiment", "in an embodiment", "according to one embodiment", and the like generally mean the particular feature, structure, or characteristic following the phrase is included in at least one embodiment of the present disclosure, and may be included in more than one embodiment of the present disclosure. Importantly, such phrases are non-limiting and do not necessarily refer to the same embodiment but, of course, can refer to one or more preceding and/or succeeding embodiments. For example, in the appended claims, any of the claimed embodiments can be used in any combination.

As used herein, the terms "% by weight", "wt. %", "weight percent", or "percentage by weight" are used interchangeably and, unless stated otherwise, are based on the total weight of the referenced composition.

The phrase "substantially free" shall be used herein to mean present in an amount less than 1 weight percent, or less than 0.1 weight percent, or less than 0.01 weight percent based on the total weight of the referenced composition.

As used herein, the term "alkyl" is inclusive of both straight chain and branched chain groups and of cyclic groups. In some embodiments, the alkyl group may have up to 40 carbons (in some embodiments up to 30, 20, 15, 12, 10, 8, 7, 6, or 5 carbons) unless otherwise specified. Cyclic groups can be monocyclic or polycyclic, and in some embodiments, can have from 3 to 10 carbon atoms.

The term "estolide", as used herein, is intended to be consistent with the definition commonly accepted in the field. However, if any inconsistencies exist, the terms "estolide" and "estolide of castor oil alkoxylate", as used throughout the present disclosure, are intended to refer to the structure defined by formula (I) and produced by the process disclosed herein.

The term "pesticide" refers to at least one pesticide selected from the group consisting of a fungicide, insecticide, nematicide, herbicide, a safener, a plant growth regulator and a mixture thereof. In one particular aspect, the pesticide is selected from the group consisting of a fungicide, insecticide, herbicide and a mixture thereof. The person skilled in the art is familiar with such pesticides, which can be found in, for example, the Pesticide Manual, 15th Ed. (2011), The British Crop Protection Council, London.

"Fungicide" means an active ingredient that kills, controls or otherwise adversely modifies the growth of a fungal pathogen. Examples of fungicides that can be employed in the present disclosure include, but are not limited to, (3-ethoxypropyl)-mercury bromide, 2-methoxyethylmercury chloride, 2-phenylphenol, 8-hydroxyquinoline sulfate, 8-phenylmercurioxyquinoline, acibenzolar, acibenzolar-S-methyl, acypetacs, acypetacs-copper, acypetacs-zinc, aldimorph, allyl alcohol, ametoctradin, amisulbrom, ampropylfos, anilazine, aureofungin, azaconazole, azithiram, azoxystrobin, barium polysulfide, benalaxyl, benalaxyl-M, benodanil, benomyl, benquinox, bentaluron, benthiavalicarb, benthiavalicarb-isopropyl, benzalkonium chloride, benzamacril, benzamacril-isobutyl, benzamorf, benzohydroxamic acid, bethoxazin, binapacryl, biphenyl, bitertanol, bithionol, bixafen, blasticidin-S, Bordeaux mixture, boscalid, bromuconazole, bupirimate, Burgundy mixture, buthiobate, butylamine, calcium polysulfide, captafol, captan, carbamorph, carbendazim, carboxin, carpropamid, carvone, Cheshunt mixture, chinomethionat, chlobenthiazone, chloraniformethan, chloranil, chlorfenazole, chlorodinitronaphthalene, chloroneb, chloropicrin, chlorothalonil, chlorquinox, chlozolinate, climbazole, clotrimazole, copper acetate, copper carbonate, basic, copper hydroxide, copper naphthenate, copper oleate, copper oxychloride, copper silicate, copper sulfate, copper zinc chromate, cresol, cufraneb, cuprobam, cuprous oxide, cyazofamid, cyclafuramid, cycloheximide, cyflufenamid, cymoxanil, cypendazole, cyproconazole, cyprodinil, dazomet, dazomet-sodium, DBCP, debacarb, decafentin, dehydroacetic acid, dichlofluanid, dichlone, dichlorophen, dichlozoline, diclobutrazol, diclocymet, diclomezine, diclomezine-sodium, dicloran, diethofencarb, diethyl pyrocarbonate, difenoconazole, diflumetorim, dimethirimol, dimethomorph, dimoxystrobin, diniconazole, diniconazole-M, dinobuton, dinocap, dinocap-4, dinocap-6, dinocton, dinopenton, dinosulfon, dinoterbon, diphenylamine, dipyrithione, disulfiram, ditalimfos, dithianon, DNOC, DNOC-ammonium, DNOC-potassium, DNOC-sodium, dodemorph, dodemorph acetate, dodemorph benzoate, dodicin, dodicin-sodium, dodine, drazoxolon, edifenphos, epoxiconazole, etaconazole, etem, ethaboxam, ethirimol, ethoxyquin, ethylmercury 2,3-dihydroxypropyl mercaptide, ethylmercury acetate, ethylmercury bromide, ethylmercury chloride, ethylmercury phosphate, etridiazole, famoxadone, fenamidone, fenaminosulf, fenapanil, fenarimol, fenbuconazole, fenfuram, fenhexamid, fenitropan, fenoxanil, fenpiclonil, fenpropidin, fenpropimorph, fentin, fentin chloride, fentin hydroxide, ferbam, ferimzone, fluazinam, fludioxonil, flumetover, flumorph, fluopicolide, fluopyram, fluoroimide, fluotrimazole, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, furcarbanil, furconazole, furconazole-cis, furfural, furmecyclox, furophanate, glyodin, griseofulvin, guazatine, halacrinate, hexachlorobenzene, hexachlorobutadiene, hexaconazole, hexylthiofos, hydrargaphen, hymexazol, imazalil, imazalil nitrate, imazalil sulfate, imibenconazole, iminoctadine, iminoctadine triacetate, iminoctadine trialbesilate, iodomethane, ipconazole, iprobenfos, iprodione, iprovalicarb, isoprothiolane, isopyrazam, isotianil, isovaledione, kasugamycin, kresoxim-methyl, mancopper, mancozeb, mandipropamid, maneb, mebenil, mecarbinzid, mepanipyrim, mepronil, meptyldinocap, mercuric chloride, mercuric oxide, mercurous chloride, metalaxyl, metalaxyl-M, metam, metam-ammonium, metam-potassium, metam-sodium, metazoxolon, metconazole, methasulfocarb, methfuroxam, methyl bromide, methyl isothiocyanate, methylmercury benzoate, methylmercury dicyandiamide, methylmercury pentachlorophenoxide, metiram, metominostrobin, metrafenone, metsulfovax, milneb, myclobutanil, myclozolin, N-(ethylmercury)-p-toluene-sulphonanilide, nabam, natamycin, nitrostyrene, nitrothal-isopropyl, nuarimol, OCH, octhilinone, ofurace, orysastrobin, oxadixyl, oxine-copper, oxpoconazole, oxpoconazole fumarate, oxycarboxin, pefurazoate, penconazole, pencycuron, penflufen, pentachlorophenol, penthiopyrad, phenylmercuriurea, phenylmercury acetate, phenylmercury chloride, phenylmercury derivative of pyrocatechol, phenylmercury nitrate, phenylmercury salicylate, phosdiphen, phthalide, picoxystrobin, piperalin, polycarbamate, polyoxins, polyoxorim, polyoxorim-zinc, potassium azide, potassium polysulfide, potassium thiocyanate, probenazole, prochloraz, procymidone, propamocarb, propamocarb hydrochloride, propiconazole, propineb, proquinazid, prothiocarb, prothiocarb hydrochloride, prothioconazole, pyracarbolid, pyraclostrobin, pyraclostrobin, pyrametostrobin, pyraoxystrobin, pyrazophos, pyribencarb, pyridinitril, pyrifenox, pyrimethanil, pyriofenone, pyroquilon, pyroxychlor, pyroxyfur, quinacetol, quinacetol sulfate, quinazamid, quinconazole, quinoxyfen, quintozene, rabenzazole, salicylanilide, sedaxane, silthiofam, simeconazole, sodium azide, sodium orthophenylphenoxide, sodium pentachlorophenoxide, sodium polysulfide, spiroxamine, streptomycin, sulfur, sultropen, TCMTB, tebuconazole, tebufloquin, tecloftalam, tecnazene, tecoram, tetraconazole, thiabendazole, thiadifluor, thicyofen, thifluzamide, thiochlorfenphim, thiomersal, thiophanate, thiophanate-methyl, thioquinox, thiram, tiadinil, tioxymid, tolclofos-methyl, tolylfluanid, tolylmercury acetate, triadimefon, triadimenol, triamiphos, triarimol, triazbutil, triazoxide, tributyltin oxide, trichlamide, tricyclazole, tridemorph, trifloxystrobin, triflumizole, triforine, triticonazole, uniconazole, uniconazole-P, validamycin, valifenalate, vinclozolin, zarilamid, zinc naphthenate, zineb, ziram, zoxamide and mixtures thereof.

"Insecticde" means an active ingredient that kills, controls or otherwise adversely modifies the growth of an insect. Examples of insecticides that can be employed in the present disclosure include, but are not limited to, 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluoron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, fufenozide, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphosmethyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, meperfluthrin, mephosfolan, mercurous chloride, mesulfenfos, metaflumizone, methacrifos, methamidophos, methidathion, methiocarb, methocrotophos, methomyl, methoprene, methothrin, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluoron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, profluthrin, promacyl, promecarb, propaphos, propetamphos, propoxur, prothidathion, prothiofos, prothoate, protrifenbute, pymetrozine, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos and mixtures thereof.

"Herbicide" means an active ingredient that kills, controls or otherwise adversely modifies the growth of a plant. Examples of herbicides that can be employed in the present disclosure include, but are not limited to, 4-CPA, 4-CPB, 4-CPP, 2,4-D, 3,4-DA, 2,4-DB, 3,4-DB, 2,4-DEB, 2,4-DEP, 3,4-DP, 2,3,6-TBA, 2,4,5-T, 2,4,5-TB, acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, diallate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dim idazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, flurtamone, fluthiacet, fomesafen, foramsulfuron, fosamine, furyloxyfen, glufosinate, glufosinate-P, glyphosate, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, orthodichlorobenzene, orthosulfamuron, oryzalin, oxadiargyl, oxadiazon, oxapyrazon, oxasulfuron, oxaziclomefone, oxyfluorfen, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazim in, thidiazuron, thiencarbazone-methyl, thifensulfuron, thiobencarb, tiocarbazil, tioclorim, topramezone, tralkoxydim, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac tritosulfuron, vernolate, xylachlor and mixtures thereof.

"Safener" means an active ingredient applied with herbicides to protect crops against their injury. Some of the safeners that can be employed in the present disclosure include, but are not limited to, benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, isoxadifen-ethyl, mefenpyr-diethyl, MG 191, MON 4660, naphthalic anhydride (NA), oxabetrinil, R29148, N-phenylsulfonylbenzoic acid amides and mixtures thereof.

"Nematicide" means an active ingredient having an effect on, such as reduction in the damage caused by, an agricultural-related nematode. Examples of nematicides which may be used in the present disclosure include, but are not limited to, an avermectin (for e.g., abamectin), carbamate nematicides (for e.g., aldicarb, thiadicarb, carbofuran, carbosulfan, oxamyl, aldoxycarb, ethoprop, methomyl, benomyl, alanycarb), organophosphorus nematicides (for e.g., phenamiphos (fenamiphos), fensulfothion, terbufos, fosthiazate, dimethoate, phosphocarb, dichlofenthion, isamidofos, fosthietan, isazofos ethoprophos, cadusafos, terbufos, chlorpyrifos, dichlofenthion, heterophos, isamidofos, mecarphon, phorate, thionazin, triazophos, diamidafos, fosthietan, phosphamidon, captan and mixtures thereof.

"Plant growth regulator" means an active ingredient used to influence the growth characteristics of plants. Examples of plant growth regulators which may be used in the present disclosure include, but are not limited to, 1-naphthaleneacetic acid, 1-naphthaleneacetic acid K-salt, 1-napthol, 2,4-dichlorophenoxyacetic acid (2,4-D), 2,4-DB, 2,4-DEP, 2,3,5-triiodobenzoic acid, 2,4,5-trichlorophenoxyacetic acid, 2-naphthoxyacetic acid, 2-naphthoxyacetic acid sodium salt, 3-chloro-4-hydroxyphenylacetic acid, 3-indoleacetic acid, 4-biphenylacetic acid, 4-chlorophenoxyacetic acid (4-CPA), 4-hydroxyphenylacetic acid, 6-benzylaminopurine, Auxindole, α-naphthaleneacetic acid K-salt, β-naphthoxyacetic acid, p-chlorophenoxyacetic acid, dicamba, dichlorprop, fenoprop, indole-3-acetic acid (IAA), indole-3-acetyl-DL-aspartic acid, indole-3-acetyl-DL-tryptophan, indole-3-acetyl-L-alanine, indole-3-acetyl-L-valine, indole-3-butyric acid (IBA), indole-3-butyric acid K-salt, indole-3-propionic acid; α-naphthaleneacetic acid, methyl indole-3-acetate, naphthaleneacetamide, naphthaleneacetic acid (NAA), phenylacetic acid, picloram, potassium naphthenate, sodium naphthenate, 4-hydroxyphenethyl alcohol, 4-CPPU, 6-benzylaminopurine (BA), 6-(Y,Y-dimethylallylamino)purine (2iP), 2-iP-2HCl, adenine, adenine hem isulfate, benzyladenine, kinetin, meta-topolin, N6-benzoyladenine, N-benzyl-9-(2-tetrahydropyranyl) adenine (BP A), N-(2-chloro-4-pyridyl)-N-phenylurea, gibberellic acid ($GA_3$), gibberellins, gibberellins A4+A7 ($GA_{4/7}$), ethylene and abscisic acid.

The term "target substrate" refers to a site underlying plant foliage which is the intended destination for the pesticide including, but not limited to, natural ground surfaces such as soil, water (for e.g. lakes, ponds, marshes, swamps, streams, puddles, etc.) and artificial surfaces (for e.g. pavement), a pest, or a combination thereof.

A "pest" generally includes an insect, mite, tick and other arthropods, a disease agent such as fungi, protozoa, bacteria and viruses, helminths, nematodes (roundworms), cestodes (tapeworms), platyhelminths (flatworms), trematodes (flukes) and other worms, sporozoan parasites, slugs and snails, and vertebrates such as birds, rodents or other vertebrates which can directly or indirectly injure or cause disease or damage in any plant or part thereof or any processed, manufactured or other product of the plant.

A "pesticidally effective amount" refers to that amount of a pesticide which, upon application, either reduces the presence of pests, or enhances a plant's resistance to a pest.

Turning to the present disclosure, it was surprisingly found that subjecting a specific ratio of castor oil and an alkoxylated glycerin to a transesterification reaction in the presence of a base catalyst produces a unique estolide of castor oil alkoxylate having relatively improved properties over similar castor oil alkoxylates prepared by direct alkoxylation.

The present disclosure is generally directed to a composition comprising an estolide produced from the transesterification reaction of castor oil and alkoxylated glycerin—otherwise referred to herein as "an estolide of castor oil alkoxylate." In particular, the present disclosure is directed to a composition comprising an estolide having a formula (I):

(I)

wherein R' is H, CH$_3$, CH$_2$CH$_3$, or a combination thereof; x, y, and z each range from 2 to 100 and the sum of x, y, and z is in a range of from 6 to 300; and R is a C$_9$ unsaturated alkyl group.

In one embodiment, R' is hydrogen. In another embodiment, x, y, and z each range from 2 to 75, or from 2 to 50, or from 2 to 25, or from 2 to 10, or from 2 to 5.

According to one particular embodiment, the sum of x, y, and z in formula (I) is in a range of from 6 to 275, or from 6 to 250, or from 6 to 225, or from 6 to 200, or from 6 to 175, or from 6 to 150, or from 6 to 125, or from 7 to 100, or from 7 to 90, or from 7 to 80, or from 7 to 70, or from 7 to 60, or from 7 to 50, or from 8 to 50, or from 8 to 45, or from 8 to 40, or from 9 to 40, or from 9 to 30, or from 5 to 30, or from 5 to 25, or from 5 to 15, or from 5 to 10, or from 10 to 25, or from 10 to 15. In a preferred aspect, the sum of x, y, and z in formula (I) is in a range of from 10 to 25.

In yet another embodiment, R' is hydrogen and the sum of x, y, and z is in a range of from 10 to 25 for formula (I).

In one embodiment, the estolide represented by formula (I) is the reaction product of castor oil and alkoxylated glycerin. The alkoxylated glycerin can be selected from ethoxylated glycerin, propoxylated glycerin, butoxylated glycerin, or combinations thereof.

Castor oil typically comprises 85 to 95 wt. % ricinoleic acid, 2 to 6 wt. % oleic acid, 1 to 5 wt. % linoleic acid, 0.5 to 1 wt. % palmitic acid, 0.5 to 1 wt. % stearic acid, and about 0.5 to 4 wt. % other acids. In one non-limiting example, the castor oil comprises 89.5 wt. % ricinoleic acid, 4.2 wt. % linoleic acid, 3.0 wt. % oleic acid, 1.0 wt. % palmitic acid, 1.0 wt. % stearic acid and 1.3 wt. % other acids. One non-limiting commercial example of castor oil is the castor oil provided by Acme-Hardesty (Blue Bell, Pa.) having a minimum ricinoleic acid content of 85 wt. %, a maximum oleic acid content of 1 wt. %, and a maximum amount of insoluble impurities of 0.02 wt. %.

In another aspect, the present disclosure is directed to a method of producing a composition comprising an estolide of castor oil alkoxylate, wherein the method comprises (i) combining a base catalyst, castor oil, and an alkoxylated glycerin to form a reactant mixture, and (ii) heating the reactant mixture at a temperature in a range of from 110° C. to 150° C.

The alkoxylated glycerin is represented by formula (II):

(II)

wherein R' is H, CH$_3$, CH$_2$CH$_3$, or a combination thereof; and x, y, and z each range from 2 to 100 and the sum of x, y, and z is in a range of from 6 to 300.

In one embodiment, R' is hydrogen. In another embodiment, x, y, and z each range from 2 to 75, or from 2 to 50, or from 2 to 25, or from 2 to 10, or from 2 to 5.

According to one particular embodiment, the sum of x, y, and z in formula (II) is in a range of from 6 to 275, or from 6 to 250, or from 6 to 225, or from 6 to 200, or from 6 to 175, or from 6 to 150, or from 6 to 125, or from 7 to 100, or from 7 to 90, or from 7 to 80, or from 7 to 70, or from 7 to 60, or from 7 to 50, or from 8 to 50, or from 8 to 45, or from 8 to 40, or from 9 to 40, or from 9 to 30, or from 5 to 30, or from 5 to 25, or from 5 to 15, or from 5 to 10, or from 10 to 25, or from 10 to 15. In a preferred aspect, the sum of x, y, and z in formula (II) is in a range of from 10 to 25.

In yet another embodiment, R' is hydrogen and the sum of x, y, and z is in a range of from 10 to 25 for formula (II).

Figure 1:
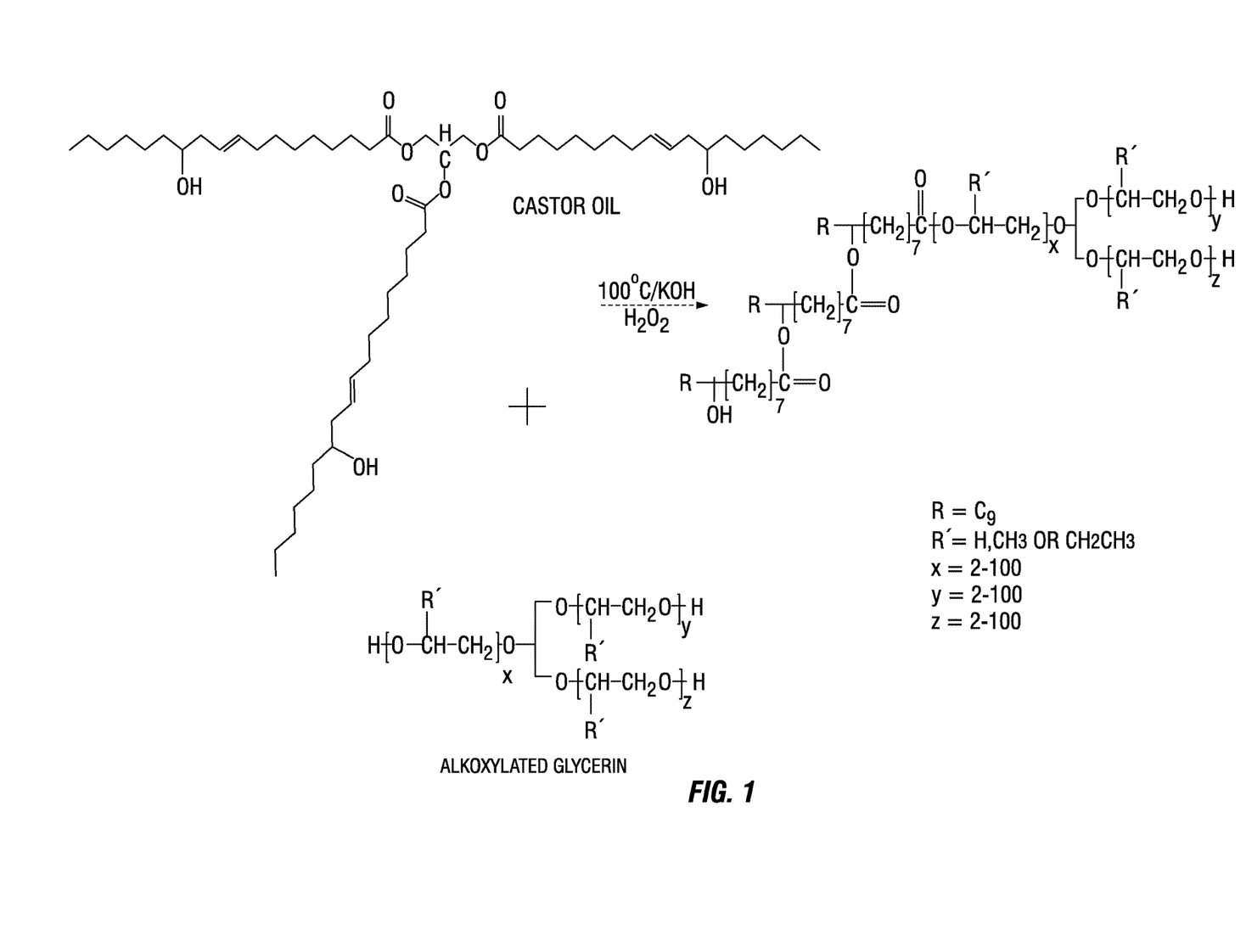
FIG. 1 is a representative illustration of the reaction mechanism for producing an estolide of castor oil alkoxylate.

A representative illustration of the method of producing the estolide of castor oil alkoxylate is shown in FIG. 1.

The castor oil is present in the reactant mixture at an amount in a range of from about 60 to about 80 wt. %, or from about 65 to about 75 wt. %, or from about 66 to about 74 wt. %, or from about 67 to about 73 wt. %, or from about 68 to about 72 wt. %, or from about 69 to about 71 wt. % based on the combined weight of the castor oil and the alkoxylated glycerin. In one aspect, the castor oil is present in the reactant mixture at about 70 wt. % based on the combined weight of the castor oil and the alkoxylated glycerin.

The alkoxylated glycerin is present in the reactant mixture at an amount in a range of from about 20 to 40 wt. %, or from about 25 to 35 wt. %, or from about 26 to about 34 wt. %, or from about 27 to about 33 wt. %, or from about 28 to about 32 wt. %, or from about 29 to about 31 wt. % based on the combined weight of the castor oil and the alkoxylated glycerin. In one aspect, the alkoxylated glycerin is present in the reactant mixture at about 30 wt. % based on the combined weight of the castor oil and alkoxylated glycerin.

In one embodiment, the alkoxylated glycerin is produced by (i) combining glycerin and an alkylene oxide, wherein the alkylene oxide is selected from the group consisting of ethylene oxide, propylene oxide, and butylene oxide, and (ii) heating the combination of glycerin and alkylene oxide at a temperature in a range of from about 120° C. to about 165° C., or from about 120° C. to about 160° C., or from about 150° C. to about 165° C., or from about 150° C. to about 160° C., or from about 155° C. to about 165° C. It is to be understood that a person of ordinary skill in the art is fully capable of determining the amount of time to heat the combination of glycerin and alkylene oxide based on (i) the targeted amount of alkoxylation and (ii) the specific heating conditions.

In one particular embodiment, the castor oil and alkoxylated glycerin are present in the reactant mixture at a weight ratio of from about 80:20 to about 60:40, or from about 75:25 to about 65:35, or at about 70:30 of castor oil to alkoxylated glycerin.

The base catalyst comprises a strong base having a pH greater than 9, or from 9 to 13, or from 10 to 13. In one embodiment, the base catalyst comprises a strong base including potassium hydroxide, sodium hydroxide, ammonium hydroxide, sodium methoxide, potassium methoxide, or combinations thereof. In one particular aspect, the base catalyst is potassium hydroxide. One non-limiting example of the base catalyst is a 45 wt. % potassium hydroxide solution commercially available from Ashta Chemicals, Inc. (Ashtabula, Ohio).

The base catalyst can be removed from the estolide composition using, for example, one or more additional processing steps such that the composition is substantially free of the base catalyst. Alternatively, the base catalyst can be allowed to remain in the reactant mixture and/or resulting estolide composition.

In one embodiment, the reactant mixture comprising the base catalyst, castor oil, and alkoxylated glycerin is heated at a temperature in a range of from about 110° C. to about 150° C., or from about 110° C. to about 140° C., or from about 130° C. to 145° C., or from about 130° C. to about 140° C. The reactant mixture is heated for a time in a range of, for example but without limitation, from about 45 minutes to 90 minutes, or from about 50 minutes to about 75 minutes, or for about 60 minutes.

The method of producing the composition comprising an estolide of castor oil alkoxylate can further comprise adding a neutralizing agent to the reactant mixture after the heating step. The neutralizing agent can comprise hydrogen peroxide, acetic acid, citric acid, or combinations thereof. In one aspect, the neutralizing agent is selected from the group consisting of hydrogen peroxide, acetic acid, citric acid, and combinations thereof.

In one particular aspect, the method of producing the composition comprises adding hydrogen peroxide to the reactant mixture after the heating step.

In another aspect, the method of producing the composition comprising an estolide of castor oil alkoxylate further comprises producing the alkoxylated glycerin prior to combining the base catalyst, castor oil, and alkoxylated glycerin.

The alkoxylated glycerin can be produced by a method comprising (i) combining glycerin and an alkylene oxide, wherein the alkylene oxide is selected from the group consisting of ethylene oxide, propylene oxide, and butylene oxide, and (ii) heating the combination of glycerin and alkylene oxide at a temperature in a range of from about 120° C. to about 165° C., or from about 120° C. to about 160° C., or from about 150° C. to about 165° C., or from about 150° C. to about 160° C., or from about 155° C. to 165° C. It is to be understood that a person of ordinary skill in the art is fully capable of determining the amount of time to heat the combination of glycerin and alkylene oxide based on (i) the targeted amount of alkoxylation and (ii) the specific heating conditions.

Another aspect of the present disclosure is directed to a cement mortar composition comprising (i) cement and (ii) the composition comprising an estolide represented by formula (I) as described herein.

Non-limiting examples of the cement include a pozzolan powder, Portland cement, slag cements, other types of conventional cements, or combinations thereof. Non-limiting examples of the pozzolan powder include Class C fly-ash, Class F fly-ash, Class N pozzolanic ash, and combinations thereof.

The cement mortar composition can further comprise at least one of an aggregate material, a thickening agent, an anti-sag agent, an air entraining agent, a wetting agent, a defoamer, a superplasticizer, a dispersant, a calcium-complexing agent, a retarder, an accelerator, a water repellant, a redispersible powder, a biopolymer, fibres, a freeze-thaw regulator, a corrosion inhibitor, a strength enhancer, a cement grinding aid, and water.

The cement mortar composition can also comprise one or more fillers in addition to the cement. Non-limiting examples of the one or more fillers include silica sand, natural sand, manufactured fine aggregate from stone production, bottom ash, slag, ground glass, recycled foundry sand, and combinations thereof.

Yet another aspect of the present disclosure is directed to a pigment dispersion comprising a pigment, a solvent, and the composition comprising an estolide represented by formula (I) as disclosed herein.

The pigment can be an inorganic pigment, organic pigment, or combinations thereof.

Non-limiting examples of the inorganic pigments include titanium oxide, iron oxide, calcium oxide, barium sulfate, aluminum hydroxide, barium yellow, cadmium red, chrome yellow, and carbon black manufactured by known methods such as contact methods, furnace methods, and thermal methods.

Non-limiting examples of the organic pigments include an azo pigment (azo lakes, insoluble azo pigments, condensed azo pigments, chelate azo pigments, etc.), a polycyclic pigment (phthalocyanine pigments, perylene pigments, perinone pigments, anthraquinone pigments, quinacridone pigments, dioxazine pigments, indigo pigments, thioindigo pigments, isoindolinone pigments, and quinofuranone pigments, etc.), a dye chelate (basic dye type chelates, acid dye type chelates), a nitro pigment, a nitroso pigment, and aniline black.

In one embodiment, the pigment comprises one or more black pigments including, for example but without limitation, (i) carbon black (C.I. Pigment Black 7) such as furnace black, lamp black, acetylene black, and channel black, (ii) metals such as copper and iron (C.I. Pigment Black 11), (iii)

metal compounds such as titanium oxide, and (iv) organic pigments such as aniline black (C.I. Pigment Black 1).

In another embodiment, the pigment comprises one or more pigments for colors other than black. Non-limiting examples of colored pigments include C.I. Pigment Yellow 1, 3, 12, 13, 14, 17, 24, 34, 35, 37, 42 (yellow titanium oxide), 53, 55, 74, 81, 83, 95, 97, 98, 100, 101, 104, 108, 109, 110, 117, 120, 128, 138, 150, 151, 153, and 183, C.I. Pigment Orange 5, 13, 17, 36, 43, and 51, C.I. Pigment Red 1, 2, 3, 5, 17, 22, 23, 31, 38, 48:2, 48:2 {Permanent Red 2B (Ca)}, 48:3, 48:4, 49:1, 52:2, 53:1, 57:1 (Brilliant Carmine 6B), 60:1, 63:1, 63:2, 64:1, 81, 83, 88, 101 (colcothar), 104, 105, 106, 108 (cadmium red), 112, 114, 122 (quinacridone magenta), 123, 146, 149, 166, 168, 170, 172, 177, 178, 179, 185, 190, 193, 209, 219 and 254, C.I. Pigment Violet (Rhodamine Lake), 3, 5:1, 16, 19, 23, and 38, C.I. Pigment Blue 1, 2, 15, 15:1, 15:2, 15:3, (phthalocyanine blue), 15:4, 16, 17:1, 56, 60, 63, and C.I. Pigment Green 1, 4, 7, 8, 10, 17, 18, and 36.

The solvent comprises water and/or organic solvents. Non-limiting organic solvents include, but are not limited to, xylene, toluene, an alcohol (for e.g., methanol, ethanol, n-propanol, iso-propanol, n-butanol, sec-butyl alcohol, tert-butyl alcohol, iso-butyl alcohol, furfuryl alcohol and tetra-hydrofurfuryl alcohol), a ketone or ketoalcohol (for e.g., acetone, methyl ethyl ketone and diacetone alcohol), an ether (for e.g., dimethyl ether and methyl ethyl ether), a cyclic ether (for e.g., tetrahydrofuran and dioxane), an ester (for e.g., ethyl acetate, ethyl lactate, ethylene carbonate and propylene carbonate), a polyhydric alcohol (for e.g., ethylene glycol, diethylene glycol, triethylene glycol, propylene glycol, tetraethylene glycol, polyethylene glycol, glycerol, 2-methyl-2,4-pentanediol and 1,2,6-hexantriol), a hydroxy functional ether of alkylene glycol (for e.g., butyl 2-hydroxyethyl ether, hexyl 2-hydroxyethyl ether, methyl 2-hydroxypropyl ether and phenyl 2-hydroxypropyl ether), a nitrogen containing cyclic compound (for e.g., pyrrolidone, N-methyl-2-pyrrolidone and 1,3-dimethyl-2-imidazolidinone), and a sulfur containing compound (for e.g. thioglycol, dimethyl sulfoxide and tetramethylene sulfone).

In one embodiment, the estolide having formula (I) is present in the pigment dispersion at a weight ratio of from about 0.001:50 to about 1:50, or from about 0.01:50 to 1:20, or from about 0.1:50 to about 1:1 of the estolide to pigment.

The pigment dispersion can further comprise one or more additives. Non-limiting examples of the one or more additives include a foaming agent, anti-foaming agent, defoamer, pH regulator, rheology modifier, freeze-thaw regulator, thixotrope, antisettling agent, dispersant, wetting agent, corrosion inhibitor, light stabilizer, heat stabilizer, adhesion promoter, anti-oxidant, biocide, leveling agent, antiblocking agent, resin, wax, coalescing agent, emulsifier surfactant, a resin, or combinations thereof.

Another aspect of the present disclosure is directed to a detergent composition containing the composition comprising an estolide represented by formula (I) as disclosed herein.

Conventional components of detergent compositions include, but are not limited to, a surfactant, bleaches and bleach activators, an enzyme and enzyme stabilizing agent, a suds booster or suds suppresser, an anti-tarnish and anti-corrosion agent, a non-builder alkalinity source, a chelating agent, an organic and/or inorganic filler, solvent, hydrotrope, optical brightener, dye, perfume, and modified cellulose ether fabric treatment agent. The fabric care agents or delivery enhancing agent of the present disclosure may be a component of or added to a detergent composition or a fabric conditioner. The detergent composition may be in the form of a granule, liquid, or tablet. Detergent compositions of the present disclosure may be made in accordance with U.S. Pat. Nos. 6,274,540 and 6,306,817, which are incorporated by reference herein in their entirety.

In one embodiment, the detergent composition comprises an estolide represented by formula (I) and at least one of a surface active agent, an enzyme, an enzyme stabilizer, a hydrotrope, a rheology modifier, an anti-redeposition polymer, an optical brightener, a preservative, a dye, and a fragrance.

The surface active agent comprises, for example but without limitation, one or more of an anionic surfactant, cationic surfactant, amphoteric surfactant, non-ionic surfactant, or combinations thereof.

The enzyme can be any suitable enzyme including, for example but without limitation, hemicellulase, peroxidase, protease, cellulase, xylanase, lipase, phospholipase, esterase, cutinase, pectinase, keratanase, reductase, oxidase, phenoloxidase, lipoxygenase, ligninase, pullulanase, tannase, pentosanase, malanase, β-glucanase, arabinosidase, hyaluronidase, chondroitinase, laccase, and known amylases, and combinations thereof. Other types of enzymes may also be included. They may be of any suitable origin, such as vegetable, animal, bacterial, fungal and yeast origin. However, their choice is governed by several factors such as pH-activity and/or stability optima, thermostability, stability versus active detergents, builders and so on. In some embodiments, the enzyme combination comprises a cocktail of conventional detersive enzymes like protease, lipase, cutinase and/or cellulase in conjunction with amylase. Detersive enzymes are described in greater detail in U.S. Pat. No. 6,579,839, which is hereby incorporated by reference herein in its entirety. In some aspects, the compositions herein contain from about 0.05% to about 2% by weight of a detersive enzyme.

Additional enzymes, amounts thereof, and non-limiting examples of enzyme stabilizers are discussed in detail in U.S. Patent Application Publication No. 2008/0234165, which is hereby incorporated by reference herein in its entirety.

It is also envisioned that the presently disclosed composition comprising an estolide represented by formula (I) can be used as an emulsifier in crop oil and/or as an emulsifier for blow agents in polyurethane production.

In still yet another aspect, there is provided a lubricating oil concentrate useful in metal forming or cutting applications which comprises the composition comprising an estolide represented by formula (I) as described herein and a base oil. Lubricating oil concentrates and their components/amounts are described in US 20150051132, the contents of which is incorporated by reference herein in its entirety. It has been surprisingly found that the composition comprising an estolide represented by formula (I) may act not only as an emulsifier to enable the formation of a stable emulsion after the lubricating oil concentrate has been diluted with water but may also impart lubricity in the concentrate formulation.

In one aspect, the composition comprising an estolide represented by formula (I) as described herein may be present in the lubricating oil concentrate in an amount of about 1% by weight to about 90% by weight, based on the total weight of the lubricating oil concentrate. In another aspect, the composition comprising an estolide represented by formula (I) as described herein may be present in the lubricating oil concentrate in an amount of about 2% by weight to about 50% by weight, based on the total weight of the lubricating oil concentrate. In a further aspect, the composition comprising an estolide represented by formula (I) as described herein may be present in the lubricating oil concentrate in an amount of about 3% by weight to about 30% by weight, or in an amount of about 4% by weight to about 25% by weight, or even in an amount of about 5% by weight to about 20% by weight, based on the total weight of the lubricating oil concentrate.

The lubricating oil concentrate of the present disclosure also includes a base oil, in some aspects, the base oil will have a kinematic viscosity in the range of from about 1 cSt to about 1000 cSt at a temperature of 40° C. In one particular aspect, the base oil is a petroleum-based oil, vegetable oil, animal-derived oil, a synthetic oil or a mixture thereof.

Examples of petroleum-based oils which may be used in the present disclosure include, but are not limited to, naphthalenic oils, paraffinic oils, crude oils, diesel oils, mineral seal oils, kerosenes, fuel oils, white oils and aromatic oils.

Examples of vegetable oils or animal-derived oils include, but are not limited to, canola oil, walnut oil, cashew nut oil, olive oil, corn oil, peanut oil, grape seed oil, oiticia oil, palm oil, rapeseed oil, fish oil, fish liver oil, sperm oil, oleic acid, bear oil, whale oil, and linseed oil.

Examples of synthetic oils include, but are not limited to, hydrocarbon oils and halo-substituted hydrocarbon oils such as polymerized and interpolymerized olefins, for example polybutylenes, polypropylenes, propylene-isobutylene copolymers, chlorinated polybutylenes, poly(1-hexenes), poly(1-octenes), poly(1-decenes), alkyl benzenes such as dodecylbenzenes, tetradecylbenzenes, dinonylbenzenes and di-(2-ethylhexyl)benzenes, polyphenyls such as biphenyls, terphenyls, and alkylated polyphenyls, and alkylated diphenyl ethers and alkylated diphenyl sulfides and derivatives, analogs and homologs thereof. Alkylene oxide polymers and derivatives thereof where terminal hydroxy groups have been modified by esterification, etherification etc. constitute another class of synthetic oils. These are exemplified by polyoxyalkylene polymers prepared by the polymerization of ethylene oxide or propylene oxide, the alkyl and aryl ethers of these polyoxyalkylene polymers such as methylpolyisopropylene glycol ethers, diphenyl and diethyl ethers of polyethylene glycol, and mono and polycarboxylic esters thereof, for example, the acetic esters, mixed $C_3$-$C_8$ aliphatic acid esters, $C_{12}$-$C_{22}$ fatty acid esters, and $C_{13}$ oxo diester of tetraethylene glycol. Simple aliphatic ethers may be used as synthetic oils, such as, dioctyl ether, didecyl ether, di(2-ethylhexyl) ether. Other synthetic oils comprise the esters of fatty acids such as ethyl oleate, lauryl hexanoate, and decyl palmitate and the esters of dicarboxylic acids such as phthalic acid, succinic acid, maleic acid, azelaic acid, sebacic acid, fumaric acid, adipic acid, linoleic acid dimer, malonic acid, alkyl malonic acids, alkenyl malonic acids with a variety of alcohols, such as butyl alcohol, hexyl alcohol, dodecyl alcohol, 2-ethylhexyl alcohol, ethylene glycol, diethylene glycol monoethyl ether, propylene glycol are also useful. Specific examples of these esters include dibutyl adipate, di(2-ethylhexyl) sebacate, di-n-hexyl fumarate, dioctyl sebacate, diisoctyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2-ethyl-hexanoic acid, and polyalphaolefins.

In one aspect, the base oil is a mixture of at least two of the oils described above.

In some aspects, the base oil may be present in the lubricating oil concentrate in an amount of about 0.5% by weight to about 97.5% by weight, based on the total weight of the lubricating oil concentrate. In another aspect, the base oil may be present in the lubricating oil concentrate in an amount of about 5% by weight to about 95% by weight, based on the total weight of the lubricating oil concentrate. In other aspects, the base oil is present in the lubricating oil concentrate in an amount greater than about 40% by weight, based on the total weight of the lubricating oil concentrate. In further aspects, the base oil is present in the lubricating oil concentrate in an amount less than about 40% by weight, based on the total weight of the lubricating oil concentrate. In still other aspects, the base oil is present in the lubricating oil concentrate in an amount of about 30% by weight to about 85% by weight, based on the total weight of the lubricating oil concentrate while in still other aspects, the base oil is present in the lubricating oil concentrate in an amount of about 5% by weight to about 30% by weight, based on the total weight of the lubricating oil concentrate.

In some aspects, the lubricating oil concentrate may optionally contain one or more additives. Such additives include, but are not limited to, a surfactant such as an anionic surfactant (for e.g. alkali, alkaline earth or ammonium salts of sulfonates, sulfates, phosphates, carboxylates, and mixtures thereof), a corrosion inhibitor such as alkaline and alkanolamine salts of organic acids, sulfonate, amine, amide, and organic borate compounds, a biocide such as o-phenylphenol, a bactericide, fungicide, algaecide, colorant, fragrance, chelating agent, pH buffering agent, solubilizer, anti-oxidant, anti-foaming agent, extreme pressure agent, water and mixtures thereof.

The lubricating oil concentrate may be prepared by admixing the composition comprising an estolide represented by formula (I) as disclosed herein with the base oil and optional additives.

In some aspects, the lubricating oil concentrate may be used "as-is" while in other aspects the lubricating oil concentrate may be diluted with water, preferably deionized water, or other aqueous solution prior to addition to an aqueous medium. In aspects where the lubricating oil concentrate is used "as is", the base oil is preferably a vegetable oil.

Surprisingly, it has been found that addition of the lubricating oil concentrate to an aqueous medium produces a stable, low foaming aqueous emulsion. According to some particular aspects, the stable, low foaming aqueous emulsion is obtained by the addition of the lubricating oil concentrate comprising the estolide represented by formula (I) as disclosed herein and an anionic surfactant to an aqueous medium, preferably deionized water.

According to one particular aspect, the lubricating component is used "as is" in a lubricating oil formulation to reduce friction and wear in moving machinery.

According to another particular aspect, the lubricating oil concentrate may be dispersed in an aqueous medium and used for a cutting or grinding process. The lubricating oil concentrate for a cutting or grinding process may be dispersed in an aqueous medium at a concentration of about 5 weight parts to about 20 weight parts of oil concentrate per 100 parts of aqueous medium (for e.g. water or deionized water) and may include the following

| Lubricating Oil Concentrate Components | Wt. % based on the total weight of the lubricating oil concentrate |
|---|---|
| Deionized Water | 20-40 |
| Base Oil | 5-25 |
| Anionic surfactant | 5-15 |

-continued

| Lubricating Oil Concentrate Components | Wt. % based on the total weight of the lubricating oil concentrate |
|---|---|
| Composition comprising an estolide represented by formula (I) | 5-15 |
| Additive(s) | 0-35 |

In one particular aspect, the lubricating oil concentrate components for use in such a cutting or grinding process may include:

| Lubricating Oil Concentrate Components | Wt. % based on the total weight of the lubricating oil concentrate |
|---|---|
| Deionized Water | 20-40 |
| Monoethanoamine | 3-8 |
| Triethanolamine | 5-10 |
| Tricarboxylic acid | 0-5 |
| Base Oil | 5-25 |
| Anionic surfactant | 5-15 |
| Composition comprising an estolide represented by formula (I) | 5-10 |
| Glycol ether | 0-5 |
| Dodecanol | 0-5 |

In yet another aspect, the composition comprising an estolide having the formula (I) of the present disclosure is included in an agrochemical formulation for application onto a target substrate to elicit a chemical or biological effect. In such aspect, the agrochemical formulation comprises (i) a pesticidally effective amount of a pesticide or a mixture of pesticides and (ii) the composition comprising an estolide having a formula (I) as described herein. According to some aspects, the composition comprising an estolide having the formula (I) is present in the agrochemical formulation at a concentration such that the pesticidal efficacy of the agrochemical formulation is enhanced as compared to a reference agrochemical formulation devoid of the composition comprising an estolide having the formula (I) but otherwise having the same ingredients as the agrochemical formulation. By "enhanced" it is to be understood that the composition comprising an estolide having the formula (I) of the present disclosure increases the performance of the active ingredients in agrochemical formulations (for e.g., a higher activity of the active ingredients for a given application rate, a lower application rate with a given effect, better uptake of the active ingredient by the target substrate, and thus advantages for a pre-emergence or post-emergence treatment, in particular the spray treatment of target substrates) as compared to agrochemical formulations that do not contain an estolide having the formula (I) of the present disclosure.

In some aspects, the composition useful in agrochemical formulations may consist of the estolide represented by formula (I) while in other aspects the composition may comprise the estolide represented by formula (I) and an auxiliary component.

Examples of auxiliary components include, but are not limited to, a solvent, liquid carrier, solid carrier or filler, anionic surfactant (for e.g. alkali, alkaline earth or ammonium salts of sulfonates, sulfates, phosphates, carboxylates, and mixtures thereof), nonionic surfactant (for e.g. alkoxylates, N-substituted fatty acid amides, amine oxides, esters, sugar-based surfactants, polymeric surfactants, and mixtures thereof), cationic surfactant (for e.g. quaternary ammonium compounds with one or two hydrophobic groups, or salts of long-chain primary amines), dispersant, emulsifier, wetter, adjuvant, solubilizer, penetration enhancer, protective colloid, adhesion agent, thickener, humectant, repellent, attractant, feeding stimulant, compatibilizer, bactericide, anti-freezing agent, crystallization inhibitor, anti-foaming agent, colorant, tackifier, binder, preservative, inorganic or organic acid to neutralize the pH, clarifier, stabilizer, fertilizer such as ammonium sulfate, urea or compound fertilizer, such as phosphorus-, potash- and nitrogen-based compound fertilizers (for e.g. P, K, N fertilizers), UV stabilizer and mixtures thereof.

According to some aspects, the composition useful in agrochemical formulations may include (i) about 0.1-99.9% by weight of an estolide represented by formula (I) and (ii) about 0.1-99.9% by weight of an auxiliary component, where the % by weight is based on the total weight of the composition. In another aspect, the composition may include (i) about 0.1-50% by weight of an estolide represented by formula (I) and (ii) about 0.1-50% by weight of the auxiliary component, where the % by weight is based on the total weight of the composition. In yet a further aspect, the composition may include (i) about 0.1-29.9% by weight of an estolide represented by formula (I) and (ii) about 70.1-99.9% by weight of an auxiliary component, where the % by weight is based on the total weight of the composition.

As described above, the composition comprising an estolide represented by formula (I) of the present disclosure enhances the bioactivity of a pesticide, thus the composition is a composition wherein, when combined with a pesticide or mixture of pesticides to form an agrochemical formulation and applied to a target substrate, achieves at least 60%, 65%, 70%, 75%, 80 or even at least 85%, or even at least 90% control. "% control," as used herein, refers to any observable measure of control of target substrate growth, which can include one or more of the actions of (1) killing, (2) inhibiting growth, reproduction or proliferation, and (3) removing, destroying, or otherwise diminishing the occurrence and activity of pests. Control can be measured by any of the various methods known in the art.

Accordingly, in another aspect, there is provided an agrochemical formulation comprising a pesticide and the composition comprising an estolide represented by formula (I) of the present disclosure (and optional auxiliary component(s)). The agrochemical formulation may be used in treating target substrates, such as those disclosed above, and refers to all forms of compositions including concentrates and spray formulations. "Spray formulations" are aqueous agrochemical formulations including all the components which it is desired to apply to the target substrate or their environment in a form and at a concentration (dilution) appropriate for spraying. Spray formulations can be made up by simple dilution of concentrates containing desired components (other than water), or by mixing of the individual components, or a combination of diluting a concentrate and adding further individual components or mixtures of components. Typically such end use mixing is carried out in the spray tank from which the formulation is sprayed or a holding tank for filling the spray tank and commonly such mixing and mixtures are called tank mixing and tank mixtures. "Concentrates" are agrochemical formulations, which may be aqueous or non-aqueous, and which are designed to be diluted with water (or a water based liquid) to form the corresponding spray formulations and include such compositions in liquid form such as solutions, emulsions or dispersions and in solid form, especially in water dispersible solid form, such as granules or powders. "Emulsifiable concentrates" are liquid "concentrates" including the pesticide and composition comprising an estolide represented by formula (I) in solution or dispersion, usually also including an emulsifier and/or surfactant, which readily emulsify on dilution in water, typically with no more than gentle stirring.

The amount of pesticide included in the agrochemical formulation of the present disclosure will vary according to a number of parameters, such as the target substrate to be treated, the area to be treated, etc. In general, a rate of application from about five grams to about four kilograms per hectare (g/ha) of pesticide may be suitable. The amount of the composition comprising an estolide represented by formula (I) in the agrochemical formulation may be from about 0.01-99% by weight, based on the total weight of the agrochemical formulation.

The agrochemical formulations of the present disclosure may be used in conventional agricultural methods. For example, the pesticide or mixture of pesticides and composition comprising an estolide represented by formula (I) may be mixed with water and/or other solvent(s) and/or fertilizers and applied post-emergence to a desired target substrate by any means, such as airplane spray tanks, knapsack spray tanks, cattle dipping vats, farm equipment used in ground spraying (for e.g., boom sprayers, hand sprayers), and the like.

As discussed above, in accordance with some aspects, the agrochemical formulation can be a concentrate composition, which can be diluted in a suitable volume of water to form a spray formulation (for e.g., a tank mix composition) for applying to the target substrate. The concentrate composition can be in liquid, solid, or semi-solid form. In at least one aspect, it is an aqueous concentrate composition.

In one particular aspect, the amount of the pesticide in the concentrate composition can be from about 1% by weight to about 80% by weight, alternatively from about 16% by weight to about 60% by weight, alternatively from 35% by weight to about 55% by weight, based on the total weight of the concentrate composition. The amount of the composition comprising an estolide represented by formula (I) in the concentrate composition may be from about 0.0001% by weight to about 20% by weight, alternatively between from about 0.001% by weight to about 15% by weight, or alternatively from about 0.01% by weight to about 10% by weight percent, or alternatively from about 0.1% by weight to about 5% by weight, or even alternatively from about 0.5% by weight to about 3% by weight, based on the total weight of the concentrate composition.

The concentrate composition can be diluted by a user with water to render a spray formulation containing from about 0.01% by weight to about 15% by weight, alternatively from about 0.1% by weight to about 5% by weight, alternatively from about 0.2% by weight to about 2% by weight of the pesticide, based on the total weight of the spray formulation. The spray formulation can typically contain from about 0.0001% by weight to about 3% by weight, alternatively from about 0.001% by weight to about 1% by weight, alternatively from about 0.01% by weight to about 0.5% by weight percent of the composition comprising an estolide represented by formula (I) of the present disclosure.

In other aspects of the present disclosure, the pesticide and composition comprising an estolide represented by formula (I) are combined to form a "ready-to-use" (RTU) spray formulation. The RTU spray formulation can be prepared by a user by diluting a concentrate composition as described above, or alternatively can be provided to the user as is. For example, the RTU spray formulation can contain from about 0.5% by weight to about 5% by weight, alternatively from about 0.75% by weight to about 3% by weight, alternatively from about 1.5% by weight to about 2.5% by weight of the pesticide, based on the total weight of the RTU spray formulation. The RTU spray formulation can contain from about 0.01% by weight to about 2.5% by weight, alternatively from about 0.2% by weight to about 2% by weight, alternatively from about 0.5% by weight to about 1% by weight of the composition comprising an estolide represented by formula (I) of the present disclosure. The balance of the RTU composition can be water.

In still yet another aspect, there is provided a method for killing or inhibiting or repelling a pest comprising the steps of providing an agrochemical formulation comprising (i) a pesticidally effective amount of a pesticide and (ii) a composition comprising an estolide represented by formula (I) of the present disclosure and optional auxiliary component(s) and contacting the agrochemical formulation and the pest.

Examples are provided below. However, the present disclosure is to be understood to not be limited in its application to the specific experiments, results, and laboratory procedures disclosed herein below. Rather, the Examples are simply provided as one of various embodiments and are meant to be exemplary and not exhaustive.

Improved Interfacial Tension, Foaming, and Surfactancy Properties

To illustrate the improved properties of the presently disclosed estolides of castor oil alkoxylates, three different estolide compositions were prepared from ethoxylated glycerin having either 10 moles, 15 moles, or 25 moles of ethoxylation, and were compared to alkoxylates produced via direct alkoxylation of castor oil and ethoxylated glycerin having 10 moles, 15 moles, and 25 moles of ethoxylation.

It should be noted that the number of moles of alkoxylation (e.g., 10 moles of ethoxylation) for alkoxylated glycerin refers to the number of stoichiometric equivalents of alkylene oxide added to one stoichiometric equivalent of glycerin. That is, for formula (II) disclosed herein, the number of moles of alkoxylation equals the sum of "x", "y", and "z". The same applies for formula (I) disclosed herein. For instance, an ethoxylated glycerin having 10 moles of ethoxylation can be represented by formula (II), wherein R' is hydrogen and the sum of x, y, and z is 10. A person of ordinary skill in the art will understand that x, y, and z do not necessarily have to be equal.

Estolide Compositions

To make the estolide compositions, three ethoxylated glycerin compositions were first produced having 10 moles, 15 moles, and 25 moles of ethoxylation. In order to clarify the process, only the procedure for producing estolides from 10 mole-ethoxylated glycerin will be set out below. A person of ordinary skill in the art will readily recognize the steps necessary to increase the moles of ethoxylation to 15 and 25.

The ethoxylated glycerin having 10 moles of ethoxylation was produced by charging 17.23 parts (weight percent) glycerin and 0.22 parts 45% potassium hydroxide (commercially available from Ashta Chemicals, Inc. (Ashtabula, Ohio)) into a clean, dry nitrogen purged reactor and heated at 100 to 115° C. for nitrogen stripping until water was present at 0.05 wt. % or less. The vessel was then heated to 145° C. Thereafter, 82.44 parts ethylene oxide was charged and reacted at 155 to 165° C. and less than 60 psig until the pressure change was less than 0.5 psig over a thirty minute period. The reactor was slowly vented and nitrogen stripped for 90 minutes at 120° C. Samples of the product were analyzed for hydroxyl number to determine if the target amount of ethoxylation was reached and corrections were made as necessary. Once the hydroxyl number was achieved, the reaction was cooled to 95° C. and 0.1 parts acetic acid were charged incrementally. The reaction product was mixed for 20 minutes and then used in an esterification reaction with castor oil.

The esterification reaction was carried out by adding 29.5 parts (weight percent) of the 10 mole ethoxylated glycerin described above with 0.6 parts 45% potassium hydroxide in a round bottom flask equipped with a heating mantle, thermocouple, overhead stirring, and nitrogen inlet. The composition was mixed while heating at 140° C. until the amount of water therein was less than 0.1%. The reaction was then cooled to 120° C. and 68.9 parts castor oil (commercially available from Acme-Hardesty Co. (Blue Bell, Pa.)) was slowly added into the flask over 60 minutes. The reaction was allowed to digest for 15 minutes before adding 1 part hydrogen peroxide to bleach the material.

Comparative Direct Alkoxylation Compositions

The comparative direct alkoxylation example having 10 moles of ethoxylation was prepared by charging 67.4 parts (weight %) of castor oil and 0.23 parts 45% potassium hydroxide to a clean, dry, nitrogen purged reactor. The material was heated to a range of 120° C. to 127° C. and dried under vacuum until the water content was less than 0.05%. After stripping, temperature was increased to 135° C. to 146° C. and 19 parts of ethylene oxide was added. The material was allowed to digest at 160° C. until a pressure drop less than 1 psig was recorded over a 30 minute period. Once the pressure drop was stabilized, the material was neutralized with glacial acetic acid.

The same procedure was followed for the comparative direct alkoxylation examples having 15 moles and 25 moles of ethoxylation.

Three separate tests were performed to analyze the properties of the estolides as compared to the compositions prepared via direct alkoxylation.

Interfacial tension: The interfacial tensions of the estolide examples and the comparative direct ethoxylation examples were tested using a KRUSS DVT50 drop volume tensiometer (KrUss GmbH of Hamburg, Germany) to test their interfacial tension with olive oil.

Figure 2:
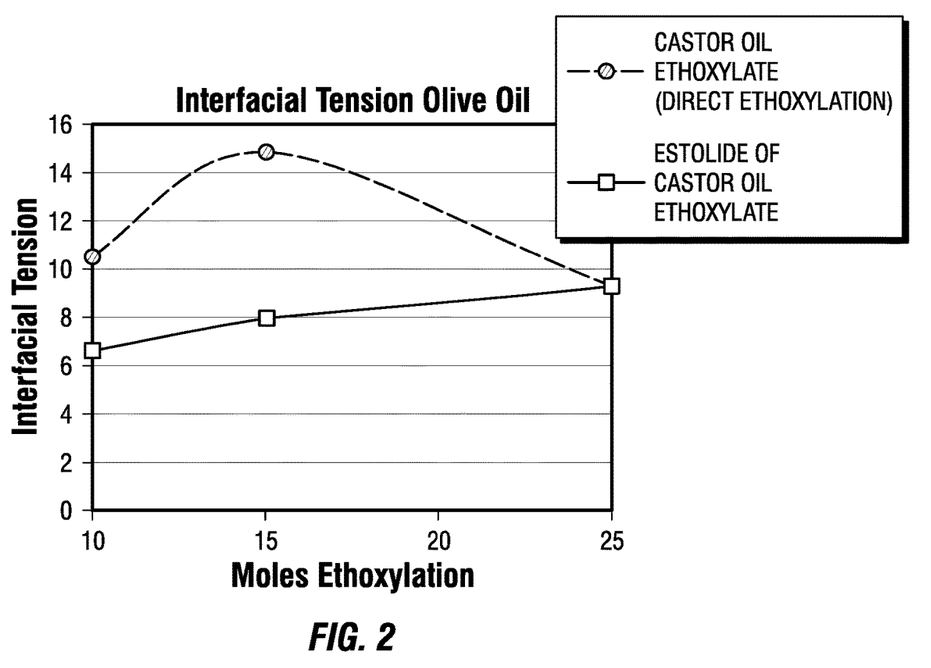
FIG. 2 is a graphical representation of the interfacial tension of an estolide of castor oil ethoxylate compared to the interfacial tension of castor oil ethoxylates produced via direct ethoxylation of castor oil.

The interfacial tension results are illustrated in FIG. 2, wherein lower interfacial tension values are preferred. As can be seen in FIG. 2, the comparative direct ethoxylation examples had significantly higher interfacial tension between 10 and 25 moles of ethoxylation when compared to the estolide examples.

Foaming: The foaming properties of the estolide examples and the comparative direct ethoxylation examples were tested by individually adding 200 mL samples of each to a Waring blender and then mixing for 10 seconds on maximum speed. Each mixed sample was then poured into separate graduated cylinders. The foam heights were measured initially and then once again after five minutes.

Figure 3:
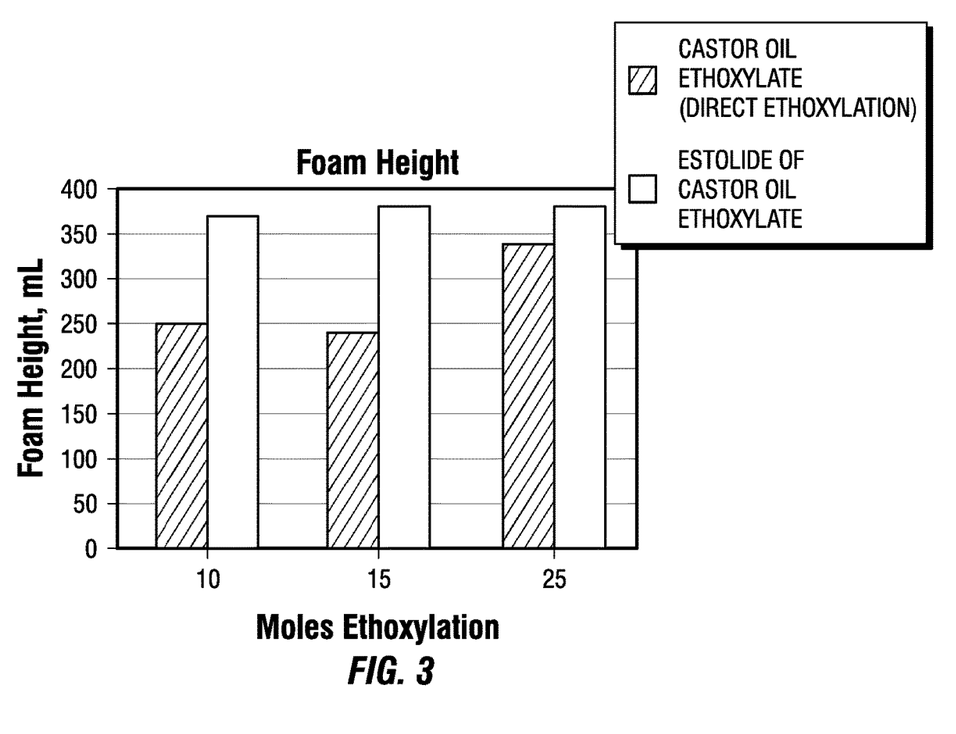
FIG. 3 is a graphical representation of the foaming properties of an estolide of castor oil ethoxylate compared to the foaming properties of castor oil ethoxylates produced via direct ethoxylation of castor oil.

The foaming properties for the estolide examples and the comparative direct ethoxylation examples are illustrated in FIG. 3, wherein the larger foam height values demonstrate better foaming properties. As can be seen in FIG. 3, the estolide examples had significantly better foam height than the comparative direct ethoxylation examples.

Surfactancy: The surfactancy (i.e., the efficiency of a wetting agent) was tested using the Draves Wetting Test following ASTM D2281 where a cotton skein was dropped into a graduated cylinder containing a surfactant solution the estolide or comparative compositions. The time required for the string connecting to the sinker and the skein to relax is recorded as the wetting time.

Figure 4:
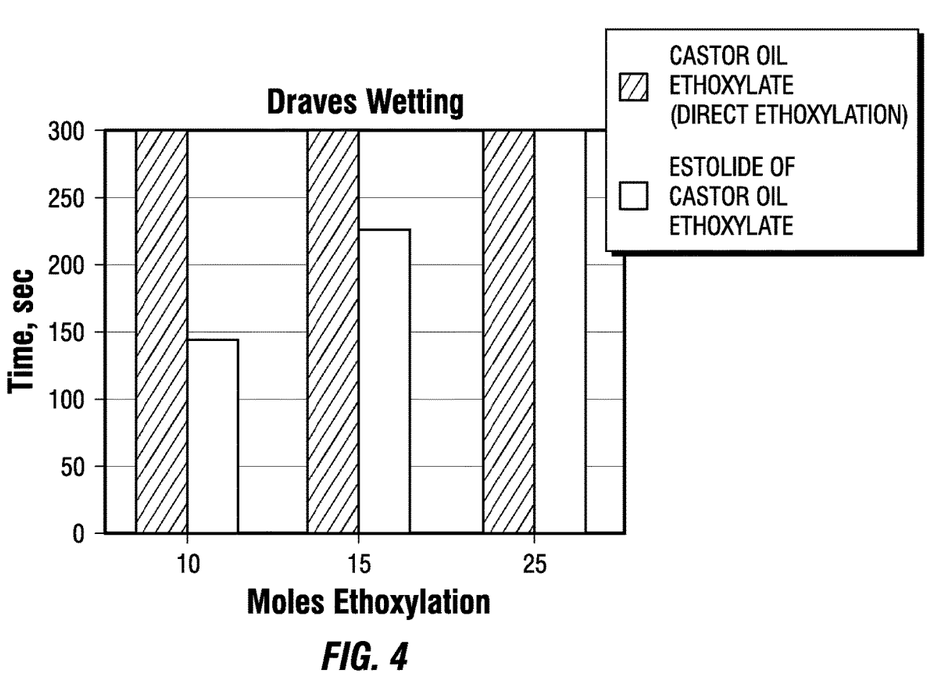
FIG. 4 is a graphical representation of the surfactancy of an estolide of castor oil ethoxylate compared to the surfactancy of castor oil ethoxylates produced via direct ethoxylation of castor oil.

The surfactancy of the estolide examples and the comparative direct ethoxylation examples are illustrated in FIG. 4, wherein lower wetting times suggest better surfactancy. As can be seen in FIG. 4, the surfactancy (or wetting time) of the estolide examples were better than the comparative direct ethoxylation examples between 10 moles and 25 moles of ethoxylation.

Mortar Flow Test

A mortar flow test according to ASTM C1437 and a mortar slump test according to ASTM C143 were also performed using a mortar comprising: a) 450 g Type I Portland Cement from Lafarge, b) 1350 g ASTM c778 test sand form local natural silica suppliers, c) Sodium Montmorillonite from Sigma Aldrich, with a measured surface area of 58 $m^2/g$, d) MIGHTY 21ES from Kao Chemical as the polycarboxylic ether (PCE), e) distilled water, and f) a clay mitigating agent (CMA) selected from either an estolide of castor oil alkoxylate or a comparative example prepared by direct alkoxylation of castor oil.

The mixture design was set to be 41% water to cement ratio, 0.14% PCE to cement ratio, 0.08% of the clay mitigating agent to cement ratio, and 0.5% clay to sand ratio. Two drops of SURFONIC® LF68 defoamer (commercially available from Huntsman Petrochemical LLC, Woodlands, Tex.) were also added to the composition as an anti-foaming agent.

The comparative example was prepared as set forth above for the comparative direct alkoxylation example having 10 moles of ethoxylation.

The estolide of alkoxylated castor oil was prepared as set forth above for the estolides produced from 10 mole-ethoxylated glycerin.

The following tables (Tables 1-3) illustrate the slump, flow, and workability of the above-described mortar when 1) not including any clay mitigation agents, 2) including the above-described comparative example prepared by direct alkoxylation as a mitigating agent, and 3) including the above-described estolide of castor oil ethoxylate as a mitigating agent. The workability value—as used herein—is the value of "slump+flow−100".

TABLE 1

| Slump (mm) | | | |
|---|---|---|---|
| | 9 min | 30 min | 60 min |
| Reference (No clay mitigating agent) | 51 | 17 | — |
| Castor Oil Direct Ethoxylation | 78 | 62 | 52 |
| Estolide of Castor Oil Ethoxylate | 80 | 77 | 68 |

TABLE 2

| Flow (mm) | | | |
|---|---|---|---|
| | 9 min | 30 min | 60 min |
| Reference (No clay mitigating agent) | 113 | 102 | — |
| Castor Oil Direct Ethoxylation | 134 | 121 | 118 |
| Estolide of Castor Oil Ethoxylate | 138 | 134 | 130 |

TABLE 3

| Workability (mm) | | | |
|---|---|---|---|
|  | 9 min | 30 min | 60 min |
| Reference (No clay mitigating agent) | 64 | 19 | — |
| Castor Oil Direct Ethoxylation | 112 | 83 | 70 |
| Estolide of Castor Oil Ethoxylate | 118 | 111 | 98 |

The reference sample in Table 1 shows the flow of the mortar without any clay mitigating agents. It is seen that due to the presence of clay in the formula, the flowability of the mortar dropped quickly within 30 minutes of observation. After adding the above-noted CMAs to the mortar, the flow was improved for the estolide example at 9 minutes, and significantly improved for the estolide example after 30 and 60 minutes, and the mortar remained flowable throughout the whole 60-minute observation period.

The slump life of the mortar was also significantly prolonged by the above-mentioned estolide example. As seen in Table 2 the slump value was improved by the castor oil direct alkoxylation example but was greatly improved by the estolide example over time.

Table 3 indicates the overall workability was improved from 9 minutes to 60 minutes by the estolide example. The estolide of castor oil alkoxylate showed much greater capacity than the castor oil direct alkoxylation molecules in promoting good slump/flowability/workability in the mortar containing clay-contaminated sand.

Pigment Dispersion Test

A pigment dispersion test was also performed using an estolide of castor oil alkoxylate as a dispersant. For comparison, the following compositions were also used as dispersants: 1) a castor oil alkoxylate produced by direct alkoxylation of castor oil, 2) a soybean oil ethoxylated glycerin produced by transesterification of soybean oil and ethoxylated glycerin (10 moles of ethoxylation) at a weight ratio of 30:70 soybean oil to ethoxylated glycerin, and 3) soybean oil ethoxylated glycerin (25 moles of ethoxylation) having a weight ratio of 30:70 of soybean oil to ethoxylated glycerin.

The dispersants were prepared using the following procedures:

The estolide of alkoxylated castor oil was prepared as set forth above for the estolides produced from 10 mole-ethoxylated glycerin.

The comparative example was prepared as set forth above for the comparative direct alkoxylation example having 10 moles of ethoxylation.

The soybean oil alkoxylated glycerin samples were prepared exactly the same as the estolide of alkoxylated castor oil using ethoxylated glycerin having 10 moles of ethoxylation and 25 moles of ethoxylation. However, the process did not produce estolides of the soybean oil alkoxylated glycerin.

Additionally, a reference dispersant was used. The reference dispersant was a leading commercial pigment dispersant, DISPERBYK® 190 dispersant, available from BYK Additives & Instruments (Wesel, Germany).

In order to test the impact of the dispersants on pigment dispersion, the dispersants were individually combined with 25% pigment (blue pigment PB 15:4 commercially available from Heliogen Blue L7101F, BASF) and water in Speedmixer™ cups (commercially available from Flacktek, Landrum, S.C.; USA). The loading was controlled at 1:10 active dispersant to pigment mass ratio.

The mixtures were then pre-mixed in a Speedmixer™ for 30 seconds and then milled with 2 mm glass beads at 3000 rpm for 3 min. The supernatant colorant was set at about 20 to 25° C. overnight, and was used to tint a base paint (i.e., PPG Olympic One Interior Semi-Gloss Enamel (Base 1-356824) at 3 wt. % of the loading in the base paint.

The tinted compositions were then letdown on a BYK BYKO coating char with a 4 mm BYK-Gardner drawdown bar. After the films dried, a BYK-Gardner spectrometer was used to evaluate their color (tint) strength.

The results of the color (tint) strength test are set forth in Table 4.

TABLE 4

| Dispersant | Color Strength |
|---|---|
| Reference Dispersant | 100% |
| Castor Oil Direct Alkoxylation | 103% |
| Estolide of Castor Oil Ethoxylate (10 moles Ethylene Oxide) | 91% |
| Soybean Oil Ethoxylated Glycerin (10 moles Ethylene Oxide) | 99% |
| Soybean Oil Ethoxylated Glycerin (25 moles Ethylene Oxide) | 102% |

Table 4 illustrates that vegetable oil alkoxylate chemistry, specifically estolides of castor oil alkoxylate, enable acceptable flowability and tinting power for the blue pigment PB 15:4 in water and in base paints. As shown in Table 4, the reference dispersant is the commercial standard and the color strength is within at least 10% of the commercial standard when using the estolide of castor oil alkoxylate described herein.

From the above description, it is clear that the present disclosure is well adapted to carry out the object and to attain the advantages mentioned herein as well as those inherent in the present disclosure. While exemplary embodiments of the present disclosure have been described for the purposes of the disclosure, it will be understood that numerous changes may be made which will readily suggest themselves to those skilled in the art which can be accomplished without departing from the scope of the present disclosure and the appended claims.

What is claimed is:

1. A composition, comprising an estolide having a formula (I):

wherein R' comprises H, $CH_3$, $CH_2CH_3$, or combinations thereof; and x, y, and z each range from 2 to 100 and the sum of x, y, and z is in a range of from 6 to 300.

2. The composition of claim 1, wherein R' is H.

3. The composition of claim 1, wherein the sum of x, y, and z is in a range of from 10 to 25.

4. The composition of claim 1, wherein the estolide is the reaction product of castor oil and alkoxylated glycerin.

5. A method of producing an estolide of castor oil alkoxylate, comprising:
combining a base catalyst, castor oil, and an alkoxylated glycerin to form a reactant mixture, wherein the alkoxylated glycerin is represented by formula (II):

wherein R' comprises H, $CH_3$, $CH_2CH_3$, or combinations thereof; and x, y, and z each range from 2 to 100 and the sum of x, y, and z is in a range of from 6 to 300, and wherein (i) the castor oil is present in the reactant mixture in a range of from 60 to 80 wt. % based on the weight of the castor oil and alkoxylated glycerin, and (ii) the alkoxylated glycerin is present in the reactant mixture in a range of from 20 to 40 wt. % based on the weight of the castor oil and alkoxylated glycerin; and heating the reactant mixture at a temperature in a range of from 110° C. to 150° C.

6. The method of claim 5, wherein the base catalyst is a strong base comprising potassium hydroxide, sodium hydroxide, ammonium hydroxide, sodium methoxide, potassium methoxide, or combinations thereof.

7. The method of claim 5, wherein (i) the castor oil is present in the reactant mixture in a range of from 65 to 75 wt. % based on the weight of the castor oil and alkoxylated glycerin, and (ii) the alkoxylated glycerin is present in the reactant mixture in a range of from 25 to 35 wt. % based on the weight of the castor oil and alkoxylated glycerin.

8. The method of claim 5, wherein R' is H.

9. The method of claim 5, wherein the sum of x, y, and z is in a range of from 6 to 25.

10. The method of claim 5, wherein the sum of x, y, and z is in a range of from 10 to 25.

11. The method of claim 5, wherein the reactant mixture is heated for a time in a range of from 45 minutes to 120 minutes.

12. The method of claim 5, further comprising adding a neutralizing agent after the step of heating the reactant mixture, wherein the neutralizing agent comprises hydrogen peroxide, acetic acid, citric acid, or a combination thereof.

13. The method of claim 5, further comprising a step of producing the alkoxylated glycerin prior to combining the base catalyst, castor oil, and alkoxylated glycerin, the step comprising:
combining glycerin and an alkylene oxide selected from the group consisting of ethylene oxide, propylene oxide, and butylene oxide, and
heating the combination of glycerin and alkylene oxide at a temperature in a range of from 120° C. to 160° C.

14. The method of claim 5, wherein the base catalyst is not removed from the composition.

15. A composition produced by the method of claim 5.

16. A cement mortar composition comprising cement and the composition of claim 1.

17. A pigment dispersion, comprising:
a pigment,
a solvent, and
the composition of claim 1.

18. A lubricating oil concentrate comprising a base oil and the composition of claim 1.

19. An agrochemical formulation comprising (i) a pesticidally effective amount of a pesticide or a mixture of pesticides and (ii) the composition of claim 1.

20. A detergent composition, comprising:
the composition of claim 1; and
at least one of a surface active agent, an enzyme, an enzyme stabilizer, a hydrotrope, a rheology modifier, an anti-redeposition polymer, an optical brightener, a preservative, a dye, and a fragrance.

* * * * *